United States Patent [19]

Alroy et al.

[11] Patent Number: 5,141,925

[45] Date of Patent: Aug. 25, 1992

[54] VIVO METHODS FOR TREATING COCCIDIOSIS

[75] Inventors: Joseph Alroy, Newton; Miercio E. A. Pereira, Chestnut Hill, both of Mass.

[73] Assignee: Trustees of Tufts College, Medford, Mass.

[21] Appl. No.: 512,351

[22] Filed: Apr. 23, 1990

[51] Int. Cl.$^5$ .................... A61K 35/78; A61K 31/73; A61K 31/195; A61K 31/70

[52] U.S. Cl. ........................ 514/23; 514/55; 514/24; 514/8; 536/4.1; 536/1.1

[58] Field of Search .......... 536/1.1, 4.1, 18.1, 536/18.2, 124, 23, 122; 514/25, 23, 54, 55, 56, 53, 279; 435/75, 169

[56] References Cited

U.S. PATENT DOCUMENTS

| | | | |
|---|---|---|---|
| 3,632,754 | 1/1972 | Balassa | 514/55 |
| 4,368,193 | 1/1983 | Argoudelis et al. | 514/24 |
| 4,431,801 | 2/1984 | Celmer et al. | 536/1.1 |
| 4,797,388 | 1/1989 | Francis | 514/23 |
| 4,868,289 | 9/1989 | Magnusson et al. | 536/4.1 |
| 4,939,123 | 7/1990 | Neeser et al. | 514/23 |
| 5,008,248 | 4/1991 | Bywater et al. | 514/23 |

Primary Examiner—Ronald W. Griffin
Assistant Examiner—Louise Leary
Attorney, Agent, or Firm—David Prashker

[57] ABSTRACT

The present invention provides a method for the prophylactic and/or therapeutic treatment of living animals susceptible to infection by at least one parasite able to cause Coccidiosis. The methodology utilizes the ability of each genus and species of infectious parasite as producing its own unique, biochemically distinct, specific lectin composition in vivo as part of the normal life cycle. The method of treatment administers a composition comprising at least one sugar to the living animal, this sugar comprising compound being able to bind selectively with the specific lectin composition of the parasite in vivo. Use of this method causes a loss of parasite infectivity and a subsequent excretion of the infectious parasite into the environment at large.

2 Claims, 1 Drawing Sheet

VIVO METHODS FOR TREATING COCCIDIOSIS

The investigations described hereinafter were supported by Tufts University.

1. Field of the Invention

The present invention is concerned generally with the veterinary treatment of diseases in domesticated animals; and is particularly directed to effective prophylactic and therapeutic treatment of coccidiosis in fowl, cattle, sheep, swine, and other animals bred and maintained for human consumption.

2. Background of the Invention

Coccidiosis is a generic name applied to a diseased condition of the digestive tract caused by parasitic protozoa of Phylum Apicomplexa, Order Coccidia. Although the order Coccidia includes the genera Toxoplasma, Sarcocystis, and Besnoitia, these genera typically cause diseases in the parenteral rather than in the intestinal organs of animals. In contrast, coccidiosis is typically limited to diseases of the digestive tract and are caused by different pathogenic species within the genera Eimeria and Isospora.

Coccidiosis outbreaks vary from severe to very mild infections; and may sometimes be so mild that no clinical or subclinical infection can be detected by measuring weight loss, feed consumption, blood parameters, or histopathology. The infectious parasitic protozoa effect the animal host in many ways depending on the tissue tropism (site organ and tissue preference) of the specific parasite; the number of parasitic oocysts ingested by the animal in the initial infection; and the pathogenicity of the parasitic species. The overwhelming majority of the pathogenic Eimeria and Isospora species are attracted to the intestinal epithelium. In severe cases, infection results in the classic symptoms of bloody diarrhea, dehydration, emaciation, and death of the animal. Often, minimal to no clinical evidence of infection is observed; but the loss to the animal is primarily as a depressed growth, impaired feed conversion, a loss of skin pigmentation, and a downgrading of quality at processing as food fit for human consumption. Representative of the most pathogenic species causing clinical Coccidiosis and its varying animal hosts are those identified within Table 1 below.

TABLE 1

| | |
|---|---|
| Chickens* | E. tenella |
| | E. necatrix |
| | E. brunetti |
| | E. maxima |
| | E. acervulina |
| | E. mitis |
| Cattle# | E. zuernii |
| | E. bovis (smithii) |
| | E. ellipsoidlis |
| Sheep# | E. arloingi A (ovina) |
| | E. weybridgensis (E. arlongis B) |
| | E. crandallis |
| | E. ahsata |
| | E. ovinoidalis |
| | E. gilruthi |
| Goats# | E. arloinigi |
| | E. faurei |
| | E. caprovina |
| | E. ninakohlyakimovae |
| | E. christenseni |
| Pigs# | Isospora suis |
| | E. debliecki |
| | E. scabra |
| | E. perminuta |

TABLE 1-continued

| | |
|---|---|
| Horses# | E. leuckarti |

*Veterinary Pharmacology and Therapeutics. (N. H. Booth and L. E. McDonald. editors), Iowa State University Press, 1988, pp 950–960.
Blood, D. C. and O. M. Radostits, Veterinary Medicine. Balliere Tindall. 7th edition, 1989, pp 993–1000.

Economically, edible fowl represent the greatest worldwide losses due to Coccidiosis infections. The current worldwide loss within the poultry industry due to these parasitic protozoa from the genus Eimeria is estimated to be about $1,800 million annually [Miller et al., in *Recent Advances In Avian Immunology Research*, Alan R. Liss, Inc., 1989, pages 117–130]. Estimated losses to other kinds of animals fit for human consumption are equally staggering. For example, in 1949, it was estimated that the annual loss to the cattle industry by Coccidiosis infections was about $10 million. The economic loss, similarly, to sheep, goats, swine, and other forms of domesticated animals are not available.

It will be noted that the financial loss from Coccidiosis is greater in chickens than with other domestic birds. Turkeys, geese, ducks, and guinea fowl also experience Coccidiosis losses. Disastrous outbreaks of renal Coccidiosis in geese have frequently been recorded. Young pigeons suffer severe mortality rates after acute attacks of diarrhea caused by Coccidial infections. Coccidiosis has also produced serious losses in pheasant and quail raised in captivity.

To more easily and completely understand the methods comprising the present invention, it is useful to summarize the structure of a typical Eimeria oocyst; and then to summarize the life cycles of a typical pathogenic species, *Eimeria tenella*, leading to the formation of sporozoites which are the infective stage for the parasite. The structure of a typical Eimeria oocyst is illustrated by FIG. 1. The oocyte wall is typically composed of inner and outer layers 100,102 and may be lined by a membrane. It may have an opening or a weak spot known as a micropyle 104 and the micropyle may itself have a cap 106. In the genus Eimeria, each sporulated oocyst has four sporocysts 108, each with two sporozoites 110. Typically, there is a refractile polar granule 112 within the oocyst; and there may be a residuum 114 of left over material as well. The sporocysts 108 may or may not have a knob, the stiedal body 116 at one end, and a substiedal body. The oocyst may also contain a sporocyst residuum 118. The sporozoites themselves are usually elongate and may contain one or more clear globules 120 of proteinaceous material.

Both sporozoites and merozoites have an apical complex including a polar ring, conoid, rhoptries, micronemes, subpellicular microtubules, and micropores. They contain stored carbohydrate in the form of amylopectin. Endoplastic reticulum, Golgi apparatus, mitochondria with tubular cristae, and ribosomes are also present. A more detailed review and description of their morphology may be obtained within the following publications: Levine, N.D., *The Coccidia* (D..M. Hammond and P. L. Long, editors), University Park Press, Baltimore, 1973, pages 1-22; Levine, N. D., *Coccidia*, University Park Press, 1970, pages 1-33; Levvine, N. D., *The Biology Of The Coccidia* (P. D. Long, editor), University Park Press, 1982, pp 1-30; and Soulsby, E. J. L., *Helminths, Arthropods, And Protozoa Of Domesticated Animals*, 7th edition, 1982, pages 594-670. See also: Levine, N. D., *Veterinary Parasitology*, Burgess Publishing Company, (1961), pages 130-232; Blood, D.

C. and O. M. Radostits, *Veterinary Medicine*, Bailliere Tindll, 7th edition, 1989, pages 993-1001; Reid et al., *Poultry Diseases*, 1988, Chapter 32, pages 692-717; and Ball et al., *Adv. Parasitol.* 28:1-54 (1989).

The life cycle of a typical parasite, *Eimeria tenella*, is illustrated by FIG. 2. The life cycles of the species within Eimeria and Isospora are very similar and thus follow a typically recognizable pattern. The oocyst, passed typically in the feces, contains a single cell, the sporont, which is not infective. This cell undergoes development (sporulation) and subsequently divides to form four sporoblasts, each of which becomes a sporocyst containing sporozoites within it. The process of sporogony or sporulation takes one day or more depending on the species, the temperature, moisture, and oxygen available. When eaten by a chicken, the oocyst wall breaks, the sporocysts are released, and the sporozoites 1 emerge. Each sporozoite 1 enters an intestinal epithelial cell 2; grows; and becomes a first generation meront or schizont 3. These meronts grow and undergo nuclear kenesis to form about 900 first generation merozoites 4, which are about 4-7 um long. These merozoites 4 break out of their host cell 5; enter new intestinal epithelial cells 6; grow; and then become second generation meronts 7,8. These, in turn, produce about 200-350 second generation merozoites 9,10 each, about 16 um long. The second generation merozoites 9,10 then break out of their host cells 11 and enter new host cells. Some of these become third generation meronts 12,13 which produce 4-30 third generation merozoites 14. The third generation merozoites 15 and a great majority of the second generation merozoites enter new host intestinal epithelial cells and start gametogony, the sexual part of their life cycles. Some become microgamonts 16,17 which each produce a large number of microgametes or male gamets 18. Others turn into macrogametes or female gamets 19,20. The macrogametes are fertilized by the microgametes and become zygotes 21 which lay down a heavy wall around themselves and turn into young oocysts. These oocysts are released from the host cell and pass out in the feces 22. The oocysts then begin to sporulate if environmental conditions permit. The sporont throws off a polar body and forms four sporoblasts 23, each of which then forms a sporocyst containing two sporozoites 24. When the sporulated oocyst 24 is ingested by another chicken, the sporozoites 1 are then again released and the life cycle begins again. For greater details regarding the various stages and entire life cycle for these paracytes, the earlier identified references are recommended.

One of the major characteristics of these parasitic species individually is their marked host and organ site specificity as indicated by Table 2 below. For example, *Eimeria tenella* typically attacks the ceca of the chicken, while *Eimeria dispersa* infects the duodenum of the turkey and quail; and *Eimeria truncata* attacks the kidneys of geese, and *Eimeria scarba* infects the large intestine of swine. Furthermore, the various targeted sites of infection (such as the different segments of mammalian or avian intestine) each have been found to provide different and individual glycoconjugates which are believed to serve as the specific recognition and adherence mechanisms for infection by the various pathogenic parasites [Mirelman, D. and I. Ofek, *Microbial Lectins And Agglutinin: Properties And Biological Activity*, John Wiley and Sons, 1986, pages 1-19; Long, P. L. and B. J. Millard, *Parasitology* 73:327-336 (1976); Etzler et al., *J. Cell Biol.* 62:329-343 (1974); and Sato, A. and S. Spicer, *Histochemistry* 73:607-624 (1982)]. Most recently, a study of different lectins as the cellular glycoconjugates of the intestinal epithelium in domestic chickens was undertaken in an effort to further study and understand the role of such lectins in the site recognition and specific adherence pattern demonstrated by these parasites [Alroy et al., *Histochem. J.* 21:187-193 (1989); Alroy et al., *Histochemistry* 86:603-607 (1987); Alroy et al., in *Diagnostic Immunohistochemistry* (R. A. DeLellif, editor), Volume 2, 1984, pages 66-88; Alroy et al., in *Advances In Immunohistochemistry* (R. A. DeLellis, editor), 1988, pages 93-131; and Debray et al. *Eur. J. Biochem.* 117:41-55 (1981)]. The infectious mechanism by which each specific parasite is able to cause clinical Coccidiosis remains a subject of considerable research and investigation.

To control the spread and pathology of Coccidiosis, particularly in poultry, only two modes of treatment appear to have come into effective use: prophylactic chemotherapy and immunological vaccination. Prophylactic chemotherapy, particularly in the poultry industry, was attempted prior to the 1940's by using various kinds of alchemic recipes, skimmed milk, vinegar, and flours of sulfur. With the discovery in the early 1940's that sulfonamides had major anticoccidial activity, drug treatment became the primary method of controlling the disease. Since that time, a large number of different anticoccidial drugs have been introduced to young chickens to reduce losses. The list presently includes: Clopidol; Quinolones; Monensin; Lasalocid; Salinomycin; Robenidine; Amprolium; Dinitolamid; Sulfonamides; Arprinocid; and Nicarbazine. This approach of chemotherapy, prophylactically and therapeutically for both fowl and mammalian animals, has resulted in the selection and survival of drug-resistant parasitic strains. Furthermore, many of the previously used and currently employed anticoccidial drugs often interfere with the host metabolism and result in toxicity or decreased weight gains and feed efficiency when used at high doses. A detailed review of the benefits and problems associated with the chemotherapeutic approach is described within *Veterinary Pharmacology And Therapeutics* (N. H. Booth and L. E. McDonald, editors) Iowa State University Press, 1988, Chapter 57; and *The Biology Of The Coccidia*, (P. L. Long, eeditor), University Park Press, Baltimore, 1982, pp 373-452.

The other major approach to containing and controlling clinical Coccidiosis has been immune vaccination. In general, exposure to a small number of coccidia oocysts will initiate an immune response; and such a controlled exposure to the more pathogenic species in domestic chickens has been practiced commercially in the U.S. for many years [S. A. Edgar, *Iowa State Col. Vet.* 17:9-11 (1956); Libby et al., *Feedstuffs* 31:18-24 and 73-74 (1959); E. E. Stuart, *Avian Disease* 4:305 (1960)]. This approach has been the basis of protection for replacement flocks and breeding hens; but has not been successful for immunizing broiler and other meat-tupe birds because of the concomittant negative effects on weight gain and feed efficiency [*The Biology Of The Coccidia*, University Park Press, 1982, p 977].

The current understanding of the role of immunoglobulins in the immune response to purposeful coccidial species infection is that circulating IgG antibody may be detected approximately seven days after initial exposure to the antigen; and that the IgG titer peaks to a maximum after about 2-4 weeks, after which time it then gradually declines. There is, however, considerably uncertainty as to the protective ability of IgG. Transfer of immunity using IgG antibodies requires large volumes and repeated injections of serum; and the results achieved are not consistent. It appears that immunity to Coccidia is not dependent on the presence of IgG antibodies in the general circulation of the animal [*Research In Avian Coccidiosis*, Proceedings Georgia Coccidiosis Conference, November 19-21, 1985].

A more likely protective role is provided by the secretory IgA antibody which is by far the most predominant immunoglobulin within the cells lining the lumen of the intestine and *lamina propria*. This IgA antibody appears to play the essential role in the protective immune response to infection with Eimeria species as well as with other genera. A major effort currently underway is to develop a multivalent subunit vaccine using antigens derived from the various stages of the parasytic life cycle. Several such antigens have been isolated and cloned; a recombinant DNA antigen using *E. coli* is apparently now under test [Kim et al., *Infect. Immun.* 57:2434-2440 (1989); Jenkins et al., *Exp. Parasitol.* 66:96-107 (1988); Danforth et al., in *Veterinary Protozoan And Hemoparasite Vaccines*, C.R.C. Press, Inc., 1989, pages 165-175; Danforth et al., *Poultry Science* 68:1643-1652 (1989)].

Insofar as is presently known, therefore, both conventionally known major approaches to treating Coccidiosis continue to impose major drawbacks and difficulties regarding their use, efficacy, and concommitant undesirable consequences. For these reasons, therefore, entirely novel methods for prophylactically and/or therapeutically treating Coccidiosis in fowl and other animals intended for consumption by humans as food have long been sought without apparent success. Accordingly, the introduction of efficacious anti-coccidiosis approaches and methods which are relatively simple, rapid, and easy to employ with large numbers of animals would be recognized by practitioners skilled in this art as a major advance and improvement in this field.

SUMMARY OF THE INVENTION

The present invention provides a method for prophylactically and/or therapeutically treating Coccidiosis in animals fit for human consumption as food. The method comprises the step of administering to the living animal a predetermined concentration of a composition comprising at least one sugar which is able to bind selectively with the specific lectin produced by the parasite of interest in vivo, the selective binding in vivo of the administered sugar comprising composition with such specific lectin as may be produced by the parasite of interest causing a decrease or loss of infectivity for the parasite.

This unique methodology relies upon the reactive interaction between the specific lectin present on the surface of the parasite during the sporozoite stage, the infectious stage of its life cycle, to bind selectively and to react with a specific sugar comprising composition; a binding which then results in the formation of non-adhering, bound sporozoites conjugated with the sugar comprising compound within the intestinal tract of the animal. These sugar-sporozoite conjugates are unable to adhere to, penetrate, or infect the host cells of the animal; and via this loss of adherence capability, are consequently excreted in the fecal matter of the host.

BRIEF DESCRIPTION OF THE FIGURES

The present invention may be more easily and completely understood when taken in conjunction with the accompanying drawing, in which.

DETAILED DESCRIPTION OF THE INVENTION

Figure 1:
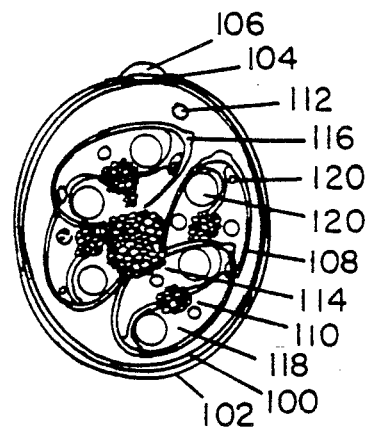
FIG. 1 is an illustration of the structure of a typical Eimeria oocyst.
Figure 2:
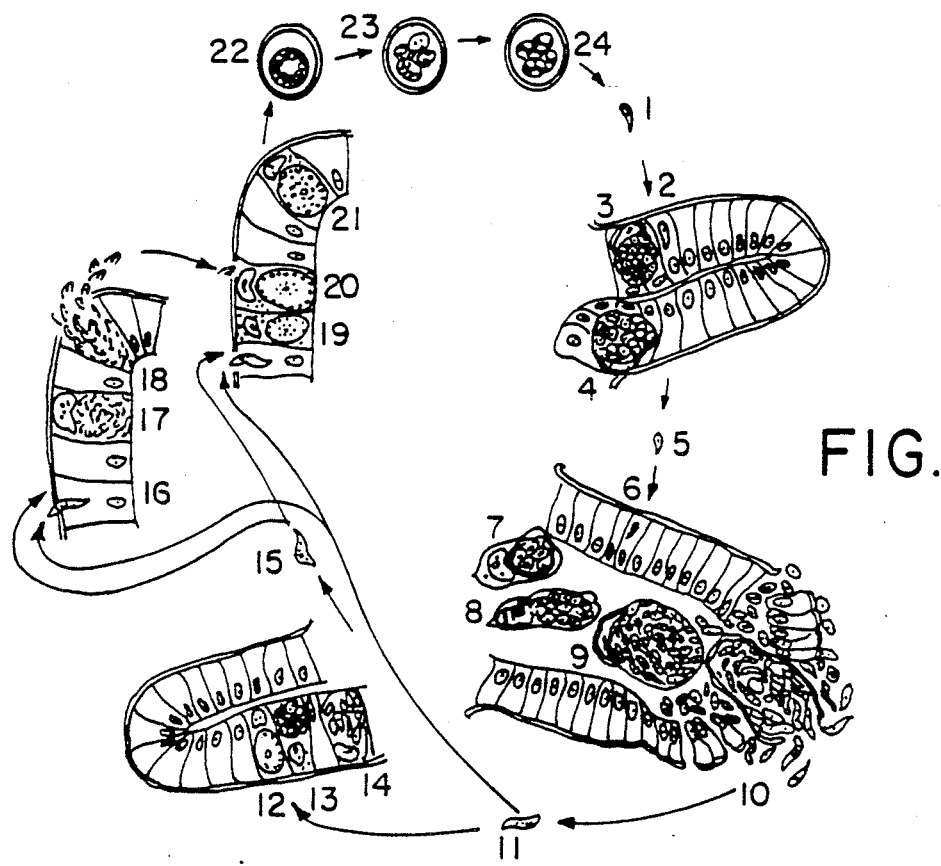
FIG. 2 is an illustration of the typical life cycle and stages of *Eimeria tenella*.

The present invention provides a method for prophylactically and/or therapeutically treating veterinary animals which are susceptible to infection by at least one parasitic protozoa within the various genera and species comprising the order Coccidia. The method employs and relies upon the only recently recognized phenomenon that each and every individual sporozoite of each species able to cause clinicial Coccidiosis produces its own, biochemically different and distinct, specific lectin composition; and by the production of its specific lectin, each individual sporozoite of each species is able to locate and adhere to its targeted, site specific host intestinal epithelial cell—via the ability of the lectin to bind specifically with only those glycoconjugates produced by the targeted individual host cell in vivo. The specific lectin composition, individually biochemically distinct for each genus and species able to cause coccidial infection, thus serves as a site recognition and adherence-selective molecule for the parasite within the intestinal tract of the animal being infected. The method of the present invention utilizes the existence of a different specific lectin composition for each genus and species of the parasite as well as the ability of the parasite during the sporozoite stage of its life cycle to produce this, biochemically distinct, specific lectin composition in vivo as the means to effectively treat and control the infectivity of the parasite itself.

Lectins, by definition, are classically recognized as a large group of different proteins widely distributed in nature which have the ability to agglutinate erythrocytes and many other types of cells. Although the existence of such compositions has been known since 1899 when a hemagglutinin was isolated from castor beans, the term "lectin" was first introduced only in 1954 [Boyd, W. C. and E. Slapleigh, *Science* 119:419 (1954)]. The term lectin is now generally recognized as designating a "sugar-binding protein or glycoprotein of non-immune origin which agglutinates cells and/or precipitates glycoconjugates" [Goldstein et al., *Nature* 285:66 (1980)]. Nearly all lectins can be bound and inhibited by free oligosaccharides or monosaccharides of appropriate specificity (formulation and structure). It is this ability of lectin compositions to bind selectively with only specific sugars or saccharides which is the underlying basis of the method comprising the present invention.

The present methodology recognizes that the infectious stage within the life cycle for the Eimeria and Isospora oocyst is the sporozoite—during which the sporozoite manufactures a unique, biochemically distinct, specific lectin composition as part of its growth. The different lectin compositions produced by each genus and species of sporozoite responsible for Coccidiosis is thus responsible for the ability of the parasite to bind to diverse segments of the host's intestinal tract and to different targeted host epithelial cells. The targeted host cell's ability to produce unique cellular glycoconjugates which vary from site-to-site in the intestine serve as the corresponding recognition and adherence basis for the individual parasites. Since each sporozoite (the form that infects the host's cells) from each species of parasite produces a distinctly different surface lectin, this difference in lectins with the corresponding differences in sugar specificities allows each species of parasite to recognize and to become adhered to only its individual targeted host cell. The range of parasites and the variety of corresponding site specific host cells presenting a glycoconjugate which will bind selectively to that genus and species of parasite is identified within Table 2 below.

TABLE 2

| SPECIES | HOST | HOST CELL SITE OF INFECTION |
|---|---|---|
| Eimeria tenella | Chicken | Ceca |
| Eimeria acervulina | Chicken | Duodenum, Upper Jejunum |
| Eimeria maxima | Chicken | Middle of the Intestine |
| Eimeria brunetti | Chicken | Lower Small Intestine, Rectum, Proximal Ceca |
| Eimeria hagani | Chicken | Upper Intestine |
| Eimeria necatrix | Chicken | Midut, Near the Yolk Sac, Diverticulum |
| Eimeria adenoeides | Turkey | Ceca, Lower Small Intestine, Rectum |
| Eimeria dispersa | Turkey, Bobwhite, Quail | Duodenum |
| Eimeria meleagrimitis | Turkey, Bobwhite, Japanese Quail | Duodenum, Upper Jejunum |
| Cryptosporidium meleagridis | Turkey | Intestine |
| Eimeria truncata | Geese | Kidney |
| Eimeria anseris | Geese | Intestine |
| Tyzzeria periciosa | Duck | Intestine |
| Eimeria labbeana | Pigeon, Dove | Intestine |
| Eimeria arlongi | Goat, Deer | Small Intestine |
| E. ninakohlyakimovae | Sheep, Goat, Deer | Small Intestine |
| Eimeria ovina | Sheep | Small Intestine |
| Eimeria parva | Sheep, Goat | Cecum, Colon |
| Eimeria bovis | Cattle | Terminal Small Intestine, Colon |
| Eimeria zuernii | Cattle | Small and Large Intestine |
| Eimeria debliecki | Swine | Jejunum, Ileum |
| Eimeria scarba | Swine | Large Intestine |
| Eimeria irresidua | Rabbit | Small Intestine |
| Eimeria magna | Rabbit | Jejunum, Ileum |
| Eimeria stiedai | Rabbit | Hepatic Bile Duct Cells |

THE METHOD OF THE PRESENT INVENTION

The improvement provided by the present invention is the intentional and purposeful administration of a composition comprising at least one sugar to the living animal. The administration may be given prophylactically—that is, prior to onset of clinically apparent coccidial infection; or therapeutically—that is, after onset of a clinically apparent coccidial infection. The sugar-comprising composition administered contains at least one sugar component which is able to bind selectively with the specific lectin produced by the parasite of interest in vivo, the consequence of which results in the parasite being unable to adhere to its targeted host cell. This, in turn, causes a meaningful decrease and/or loss of infectivity for that parasitic species in vivo; and the non-adhering, bound sugar—parasite complex is excreted out of the host's intestine via the fecal matter, thereby interrupting the infectious normal life cycle for the parasite.

It is intended that a diverse and broad membership will constitute the class of compositions comprising at least one sugar employed for both prophylactic and therapeutic purposes using the present methodology. The class of sugar comprising compositions encompasses and embraces: all sugars or saccharides of varying formulation and steroscopic (isomeric) structure and includes monosaccharides, disaccharides, and polysaccharides without regard to size or source of origin; linked or conjugated compounds of mixed chemical composition having at least one discrete sugar moiety available for binding/reaction including glycopeptides, glycolipids, and other glycoconjugates without regard to whether these are naturally occurring or synthetically produced; complex or indeterminate formulations and structures of organic matter having at least one identifiable sugar moiety or component including carbohydrates, nucleic acids, mucopolysaccharides, and the like.

With regard to the binding specificity and affinity of the sugar component or moiety itself, both the specificity and affinity are controlled by the corresponding lectin produced by the individual genus and species of parasite itself. For example, even with the most simple sugar formulations and structures, there is considerable control of specificity and affinity via the individual isomeric forms conventionally known. Thus, among simple sugars, those having only four carbon atoms provide the individual isomers of threose and erythrose; while five carbon sugars yield the isomers of lyxose, xylose, arabinose, and ribose; and six carbon sugars include talose, galactose, idose, gulose, mannose, glucose, altrose, and allose. Accordingly, a specific lectin binding selectively with only a six carbon sugar moiety will bind in the largest degree and with the greatest affinity to one individual isomer of the six carbon sugar family; nevertheless, it is expected that the same specific lectin may also demonstrate some binding capability, albeit with much less affinity, for another isomeric form of a six carbon sugar. Hence, while the binding reaction between the sugar component in the administered composition and the specific lectin produced by the parasite of interest is said to be selective, the degree of binding and the affinity of the lectin for the sugar moiety may be variable.

It is preferable in most instances that a larger sized molecule rather than a smaller sized molecule comprising at least one sugar be employed for administration. Larger and more complex compositions provide a three-dimensional structure which tends to hold the sugar moiety in a more rigid and consistent positioning, thus providing fewer degrees of rotational freedom for the sugar moiety. This is believed to provide a more rapid rate of selective binding between the sugar-comprising composition as a whole and the specific lectin found on the surface of the parasite.

In addition, it is also more desirable to administer a sugar comprising composition which contains more than one molecule of the sugar able to selectively bind with the specific lectin. Thus, an administered composition having a greater percentage or concentration of that specific sugar component is preferable to a similar compound having a smaller percentage or concentration of the requisite sugar moiety.

Administration Of The Composition Able To Bind Selectively With A Specific Lectin According to the method of the present invention, the sugar comprising composition administered to the living animal need only be introduced in such a way that the sugar is present within the intestinal tract of the animal in a relatively intact form such that it may bind to such lectin as has been produced by the parasitic species while within the gut of the animal. To achieve this purpose most easily and economically, it is most preferable that the typical feed mixture given to that animal for its normal growth and maintenance nutritionally first be mixed with sufficient concentrations and quantities of each sugar containing composition to be administered.

For this reason, recognizing that the most common pathogenic species for chickens are E. tenella, E. acervulina, and E. maxima it is recommended that the glycoproteins of fetuine, bovine submaxillary mucin, and hog gastric mucin; and/or the monosaccharide fucose and/or the carbohydrate chitotetrose be mixed with the normal feed given to chickens generally. Similarly, if the animals to be protected are cattle, it is recommended that the specific sugars and/or glycopeptides able to bind selectively with the lectins of E. bovis and E. zuernii be admixed with the normal corn, maize, or other feed normally given to cattle as part of their diet. Correspondingly, in order to produce swine herds, the specific sugars able to selectively bind with the lectins of E. debliecki and E. scarba would be introduced into the feed mixtures prepared for the swine herds.

It is expected that great differences in the affinities, purity, concentration, and dosages of the binding sugars, individually and in admixture will be encountered when used as additives to the feed given to the living animals. In general, however, it is expected that a useful concentration of sugar comprising composition can be easily determined by the user to provide efficacious dosages in the intestinal tract of the animal individually. Moreover, it is expected that each sugar comprising composition will not be used in similar quantities and that the animal handler may wish to add a range of different sugar comprising compositions in different quantities or ratios depending upon the history of coccidial infection previously known for that flock or herd, that geographic local, or the history of specific parasitic species which have been encountered within that environment previously. Such "custom mixing" is highly recommended and appropriate when specific species of parasites have been previously identified.

In the alternative, any other means for introducing a composition comprising at least one sugar into the intestinal tract of the living animal is also deemed suitable for use when practicing the method of the present invention. Although these other methods are frequently less desirable than admixture with the nutritious feed for the animal, all alternative modes of administration are within the scope of the present invention. Other means of administration typically include admixture of the sugar comprising composition in the liquids consumed by the animal. In view of the requirement that the sugar moiety in the composition be relatively intact chemically and be present in a sufficient concentration within the intestinal tract of the animal in order to selectively bind with the specific lectins produced by the parasites in vivo, it is not recommended that parenteral injection or topical modes of application be used at all. Moreover, it is expected that the administration of at least one sugar comprising composition, and preferably a mixture of different sugar containing compositions—each able to bind selectively with one lectin composition produced by an individual parasitic species, will fulfill the long term duration requirement of Coccidiosis disease control by solid food or by liquid administration to the living animal as the most desirable mode of administration.

Method For Identification Of Specific Lectin In A Parasite Of Interest From The Order Coccidia And Characterization Of Its Sugar Specificity By the representative listing of parasitic species given within Table 2 above, it is clear that a large number of different specific lectins are produced by the individual species forming the Eimeria and Isospora genera; and consequently, that a comprehensive listing of the corresponding compositions comprising at least one sugar would be several times larger than the list of parasitic species themselves. For these reasons, it is deemed valuable to provide an assay technique by which the user can determine both the chemical identity of the specific lectin produced by the parasite of interest; and to provide an assay by which the sugar specificity can be individually determined and characterized.

The lectin activity is preferably determined by a hemagglutination assay of rabbit erythrocytes. It is desirably performed in "U" well microtiter plates using lysates prepared from the parasites of interest. The sporozoites of the parasite of interest are washed three times in phosphate buffered saline (PBS), and adjusted to a concentration of $1 \times 10^7$/ml. They are lysed by sonication in "Branson" sonicator; cleared of particulate material by filtration; and assayed for lectin activity using a conventionally known hemagglutination assay. In this assay, 2% rabbit erythrocytes in PBS are added to serial doubling dilutions of the prepared test lysate in PBS containing 2 mg/ml of bovine serum albumin (BSA) and incubated at 23° C. (i.e., room temperature) for 1 hour. Lectin titer is defined as the reciprocal of the highest agglutinating dilution as determined by direct observation, which is defined as one agglutinating unit.

Sugar specificity and characterization is determined by a standard hemagglutination inhibition assay. 2% rabbit erythrocytes are added to serial doubling dilutions of the sugar-comprising test compound in PBS containing 2 mg/ml BSA and 4 hemagglutination units of lectins; followed by incubation at room temperature for 60 minutes. The minimum inhibitory concentration of the test compound is defined as the minimum concentration which is required for inhibiting 4 hemagglutination units of lectins. The following represent examples of suitable test compounds: (1) glycoproteins such as fetuine, bovine submaxillary mucin, hog gastric mucin, and -1- acid glycoprotein; (2) monosaccharides such as arabinose, fucose, glucose, galactose, mannose, N-acetylglucosamine, and N-acetylgalactosamine and their derivatives; and (3) oligosaccharides including chitobiose and chitotetrose.

To demonstrate the efficacy and value of the novel method comprising the present invention for prophylactic and/or therapeutic treatment of Coccidiosis, a variety of experiments will now be described. It will be clearly understood, however, that these experiments and the empirical data given are merely representative of the general conditions, uses, and advantages provided by the present invention; and merely serve to illustrate the variety of different genera and species of parasites, operative conditions, and divergent applications with which the defined methods can be usefully employed. Under no circumstances, however, are the specific test conditions or the empirically obtained results to be deemed as restricting or limiting the present invention in any manner.

EXPERIMENTAL SERIES

A series of experimental assays were performed to measure the in vitro inhibition of Coccidia infections by compositions comprising at least one sugar. The inhibition assay is one developed by Schmatz et al. [*J. Protozology* 33:109-114 (1986)] in which inhibition of sporozoite development is correlated with a decrease in $^3H$ uracil uptake by the host cells.

Assay Procedure

Sporozoites are excysted aseptically from sterile coccidis oocysts, cleaned of debris by passage through a cellulose or glass wool column, counted, and diluted to a concentration of approximately $2.5 \times 10^5$ sporozoites per ml.

The sporozoites are then pretreated for one hour in cell culture nutrient (Waymouth's MAB 87/3, without serum) containing various concentration of inhibiting sugars, such as 0.1, 1.0, and 10.0 mg/ml fetuine, before being inoculated onto 24-48 hour primary cultures of embryonic chick kidney cells prepared in 24 or 96 well plates. Treatment with the inhibiting sugar, such as fetuine, is continuous at the tested concentration during the incubation period, allowing the parasite development to proceed for 48 or 96 hours. Nutrient is changed every 48 hours. Because parasites developing in cell culture, but not the host cells, take up $^3H$ uracil, add 2 u Ci to each well in a 96 well plate 18 to 24 hours beore counting by liquid scintillation. Nutrient is removed from the parasitized cell cultures which are then treated with PBS solution, pH 7.6-7.8, containing 0.5% trypsin and 0.022% EDTA to detach the cells from the culture vessel, and harvested with a PHD Cell Harvester (Cambridge Instrument) onto glass fiber filter discs. Individual discs are placed into scintillation vials with 3.5 ml Toluene (plus 5.262 grams per 4 liters of PPO [2,5-diphenyloxazole]) and samples are then counted in a Beckman scintillation counter.

Similar cell cultures may be prepared on cover glasses in 6 or 24 well plates and the appropriate time periods of 48 or 96 hours, the cultures are fixed in methanol, stained with Giemsa's stain, and the parasites counted per 1,000 host cells for visual comprison of parasite development.

Results

The empirical data and results are presented in summary format by Tables E1 and E2 respectively.

TABLE E1

Lowest Concentration (mg/ml) of Glycoproteins, Monosaccharides, and Carbohydrates that Inhibited Lectin Agglutination of Three Species of Eimeria (Coccidia)

| Sugar (mg/ml) | E. tenella | E. acervulina | E. maxima |
|---|---|---|---|
| Glycoproteins | | | |
| Fetuin | 0.078 | 0.13 | 0.4 |
| Bovine Submaxillary Mucin (BSM) | 0.083 | 0.03 | NT |
| Hog Gastric Mucin | 0.125 | 0.5 | NT |
| Acid Glycoprotein | 1.25 | 0.5 | NT |
| Monosaccharides | | | |
| Arabinose | — | 25.0 | — |
| L(—)-Fucose | 1.25 | — | — |
| P-Nitro-o-D-Glucoside | 12.5 | — | — |
| 1-o-$CH_3$-D-Glucoside | 4.1 | — | — |
| Carbohydrates | | | |
| Chitobiose | 1.25 | NT | NT |
| Chitotetrose | 0.03 | NT | NT |
| Optimum pH for Lectin Activity | 08.5-9.0 and 10.5-11.0 | 7.0-7.5 and 11.0-11.5 | 8.0-8.5 |

NT = not tested

TABLE E2

Inhibition of *E. tenella* Development (96 hours) By Fetuin in Cell Culture ($^3H$ uracil by Schmatz et al.)

| | Scintillation Counts (24 hr)* | |
|---|---|---|
| Treatment | Trial 1 | Trial 2 |
| 1. Host Cells Only | 6,179.8 | 1,430.7 |
| 2. Host Cells + Parasite — No Fetuin | 16,122.0 | 2,118.4 |
| 3. Host Cells + Parasite + 5 mg/ml Fetuin | 8,135.0 | 1,394.7 |
| 4. Host Cells + Parasite + 10 mg/ml Fetuin | 8,625.6 | 1,556.4 |
| 5. Host Cells + Parasite + 15 mg/ml Fetuin | 4,328.3 | 796.1 |
| 6. Host Cells + 15 mg/ml Fetuin No Parasite | 7,826.4 | 1,942.7 |

*Counts are the mean values for eight cultures in each instance.

The lowest concentration (mg/ml) of compositions comprising at least one sugar that inhibited *E. tennella*, *E. acervulina*, or *E. maxima* are shown in Table E1. Clearly, the empirical data reveals that individual glycoproteins, monosaccharides, and carbohydrates each meaningfully inhibit these parasitic species.

In addition, the data of Table E2 reveal substantial reductions in $^3H$ uracil uptake by host cells when treated with the glycoprotein, fetuine, thus inhibiting the development of *E. tennella*. The inhibition by this parasitic species is thus equivocally demonstrated.

The present invention is not to be restricted in form nor limited in scope except by the claims appended hereto.

What we claim is:

1. An in-vivo method for treating a living animal susceptible to infection by lectin-producing parasites able to cause Coccidiosis, said method comprising the steps of:

orally administrating to the intestinal tract of said susceptible living animal an effective amount of a glycoprotein selected from the group consisting of fetucine, bovine submaxillary mucin, hog gastric mucin, and acid glycoprotein, said glycoprotein being able to bind selectively with such specific lectin as may be produced by said parasite in-vivo; and allowing said orally administered glycoprotein to bind selectively with such specific lectin as may be produced by said parasite within said intestinal tract, said selective binding causing a decrease of infectivity for said parasite in-vivo.

2. An in-vivo method for treating a living animal susceptible to infection by lectin-producing parasites able to cause Coccidiosis, said method comprising the steps of:

orally administrating to the intestinal tract of said susceptible living animal an effective amount of a carbohydrate selected from the group consisting of chitobiose and chitotetrose, said carbohydrate being able to bind selectively with such specific lectin as may be produced by said parasite in-vivo; and allowing said orally administered glycoprotein to bind selectively with such specific lectin as may be produced by said parasite within said intestinal tract, said selective binding causing a decrease of infectivity for said parasite in-vivo.

* * * * *